(12) United States Patent
Dueri et al.

(10) Patent No.: US 6,428,747 B1
(45) Date of Patent: Aug. 6, 2002

(54) INTEGRATED EXTRACORPOREAL BLOOD OXYGENATOR, PUMP AND HEAT EXCHANGER SYSTEM

(75) Inventors: Jean-Pierre Dueri, Sunnyvale; Robert Jochim, Dublin; Alex Leynov, Walnut Creek, all of CA (US)

(73) Assignee: Cardiovention, Inc., Santa Clara, CA (US)

( * ) Notice: Subject to any disclaimer, the term of this patent is extended or adjusted under 35 U.S.C. 154(b) by 0 days.

(21) Appl. No.: 09/430,219

(22) Filed: Oct. 29, 1999

Related U.S. Application Data

(63) Continuation-in-part of application No. 09/223,676, filed on Dec. 30, 1998.

(51) Int. Cl.$^7$ .......................... A61M 37/00; A61M 1/14; A61N 1/36
(52) U.S. Cl. ........................... 422/46; 422/48; 604/4.01; 604/6.13; 604/6.14
(58) Field of Search ..................... 422/44–48; 604/4.01, 604/6.09, 6.11, 6.13, 6.14; 96/4, 7–11, 243, 267–69, 303–305, 355–360, 361; 210/321.81, 321.9, 321.72, 321.78, 321.87, 500.23, 348, 456, 257, 295, 433.1

(56) References Cited

U.S. PATENT DOCUMENTS

| | | | | |
|---|---|---|---|---|
| 5,124,127 A | * | 6/1992 | Jones et al. | |
| 5,240,677 A | * | 8/1993 | Jones et al. | |
| 5,906,741 A | * | 5/1999 | Elgas et al. | |
| 6,117,390 A | * | 9/2000 | Corey, Jr. | |
| 6,224,829 B1 | * | 5/2001 | Piplani et al. | |

* cited by examiner

*Primary Examiner*—Mark Bockelman
*Assistant Examiner*—P M Bianco
(74) *Attorney, Agent, or Firm*—Fish & Neave; Nicola A. Pisano

(57) ABSTRACT

An integrated blood pump, oxygenator and heat exchanger is provided having a rotating hollow fiber bundle assembly. A plurality of vanes arranged along a central shaft of the device increase pressure near the center of the fiber bundle to develop sufficient pressure head to pump the blood through the heat exchanger. In alternative embodiments, the heat exchanger comprises a pleated metal wall, a bundle of non-permeable hollow fibers, or a coiled tub disposed between the rotating hollow fiber bundle and an interior wall of the housing.

13 Claims, 4 Drawing Sheets

INTEGRATED EXTRACORPOREAL BLOOD OXYGENATOR, PUMP AND HEAT EXCHANGER SYSTEM

REFERENCE TO RELATED APPLICATIONS

This application is a continuation-in-part of U.S. patent application Ser. No. 09/223,676, filed Dec. 30, 1998.

FIELD OF THE INVENTION

The present invention relates to integrated extracorporeal oxygenation and pumping systems having an integrated heat exchanger.

BACKGROUND OF THE INVENTION

Each year hundreds of thousands of people are afflicted with vascular diseases, such as arteriosclerosis, that result in cardiac ischemia. For more than thirty years, such disease, especially of the coronary arteries, has been treated using open surgical procedures, such as coronary artery bypass grafting. During such bypass grafting procedures, a sternotomy is performed to gain access to the pericardial sac, the patient is put on cardiopulmonary bypass, and the heart is stopped using a cardioplegia solution.

Recently, the development of minimally invasive techniques for cardiac bypass grafting, for example, by Heartport, Inc., Redwood City, Calif., and CardioThoracic Systems, Inc., Cupertino, Calif., have placed a premium on reducing the size of equipment employed in the sterile field. Whereas open surgical techniques typically provide a relatively large surgical site that the surgeon views directly, minimally invasive techniques require the placement of endoscopes, video monitors, and various positioning systems for the instruments. These devices crowd the sterile field and can limit the surgeon's ability to maneuver.

At the same time, however, the need to reduce priming volume of the oxygenator and pump, and the desire to reduce blood contact with non-native surfaces has increased interest in locating the oxygenator and pump as near as possible to the patient.

In recognition of the foregoing issues, some previously known cardiopulmonary systems have attempted to miniaturize and integrate certain components of cardiopulmonary systems. U.S. Pat. Nos. 5,266,265 and 5,270,005, both to Raible, describe an extracorporeal blood oxygenation system having an integrated blood reservoir, an oxygenator formed from a static array of hollow fibers, a heat exchanger, a pump and a pump motor that is controlled by cable connected to a control console.

The systems described in the foregoing patents employ relatively short flow paths that may lead to inadequate gas exchange, due to the development of laminar flow zones adjacent to the hollow fibers. U.S. Pat. No. 5,411,706 to Hubbard et al. describes one solution providing a longer flow path by recirculating blood through the fiber bundle at a higher flow rate than the rate at which blood is delivered to the patient. U.S. Pat. No. 3,674,440 to Kitrilakis and U.S. Pat. No. 3,841,837 to Kitrilakis et al. describe oxygenators wherein the gas transfer surfaces form an active element that stirs the blood to prevent the buildup of boundary layers around the gas transfer surfaces.

Makarewicz et al., "New Design for a Pumping Artificial Lung," *ASAIO Journal*, 42(5):M615–M619 (1996), describes an integrated pump/oxygenator having a hollow fiber bundle that is potted between an inlet gas manifold and an outlet gas manifold. The fiber bundle is rotated at high speed to provide pumping action, while oxygen flowing through the fiber bundle oxygenates the blood. Like the device described in Ratan et al., "Experimental evaluation of a rotating membrane oxygenator," *J. Thoracic & Cardio. Sura.*, 53(4):519–526 (1967), a separate heat exchanger must be used for cooling the blood.

U.S. Pat. No. 5,830,370 to Maloney et al. describes a device having a fiber bundle mounted for rotation between a fixed central diffuser element and an outer wall of a housing. The fiber bundle is rotated at speeds sufficiently high to cause shear forces that induce turbulent flow within the blood. Rotation of the fiber bundle is also used to augment heat exchange between the blood and a coolant surrounding a portion of the blood reservoir. The limited heat transfer surface area provided in such designs, however, may be insufficient to provide adequate cooling.

Other patents for systems having stationary fiber bundles also have addressed the role of the heat exchanger in an integrated assembly. For example, U.S. Pat. No. 3,768,977 to Brumfield et al. describes a blood oxygenator in which gas exchange and temperature regulation occur in the same chamber to reduce the risk of gas bubble evolution and gas embolism stemming from elevated blood temperatures. U.S. Pat. No. 4,791,054 to Hamada et al. describes an integrated heat exchanger and blood oxygenator that uses hollow fibers, formed of an organic material, as the heat transfer tubes. U.S. Pat. No. 5,770,149 to Raible et al. describes an integrated blood pump, heat exchanger, and membrane oxygenator in which heat exchange occurs after pumping but before oxygenation.

Although the devices having rotating fiber bundles described in the foregoing references offer some desirable features, such as low priming volume and low surface area, it is unclear whether such devices can provide adequate heat exchange capability, due to either limited heat transfer area or inadequate pump head to provide flow through a separate heat exchanger over a wide range of flow rates.

In view of the foregoing, it would be desirable to provide an integrated extracorporeal blood oxygenator, pump and heat exchanger having a rotating fiber bundle that provides compact size, low priming volume, low surface area and adequate temperature regulation.

It also would be desirable to provide an integrated extracorporeal blood oxygenator, pump and heat exchanger with a hollow fiber bundle having a rotating fiber bundle, and also providing adequate heat transfer area between the blood and the coolant to facilitate regulation of the blood temperature.

It further would be desirable to provide an integrated extracorporeal blood oxygenator, pump and heat exchanger having a rotating hollow fiber bundle that provides adequate pump head to account for pressure head losses in the heat exchanger over a wide range of blood flow rates.

SUMMARY OF THE INVENTION

In view of the foregoing, it is an object of the present invention to provide an integrated extracorporeal blood oxygenator, pump and heat exchanger having a rotating fiber bundle that provides compact size, low priming volume, low surface area and adequate temperature regulation.

It is another object of the present invention to provide an extracorporeal blood oxygenator, pump and heat exchanger with a hollow fiber bundle having a rotating fiber bundle and also having adequate heat transfer area between the blood and the coolant to facilitate regulation of the blood temperature.

It is yet another object of this invention to provide an integrated extracorporeal blood oxygenator, pump and heat exchanger having a rotating hollow fiber bundle that provides adequate pump head to account for pressure head losses in the heat exchanger over a wide range of blood flow rates.

These and other objects of the invention are accomplished by providing an integrated extracorporeal blood oxygenator, pump and heat exchanger, suitable for use within a sterile field, that has a low priming volume and low surface area. In accordance with the principles of the present invention, the oxygenator, pump and heat exchanger system includes a rotating hollow fiber bundle assembly that both oxygenates the blood and develops sufficient pressure head to pump the blood through an integral heat exchanger in fluid communication with the blood flow path. In addition, heat exchanger has a compact size but provides sufficient heat transfer area to facilitate temperature regulation of blood flowing through the device.

In one preferred embodiment, the heat exchanger comprises a metal waffle-like wall disposed in a separate compartment of the housing, so that blood passes along one side of the wall while coolant passes along the opposite side of the wall. In an alternative embodiment, the heat exchanger comprises a stationary bundle of non-permeable hollow fibers through which blood flows, while a coolant passes along the exterior of the bundle.

In yet another alternative embodiment, the heat exchanger comprises a coiled metal tube disposed in a housing between the rotating fiber bundle and the housing wall. Coolant passes through an interior lumen of the coiled tube to absorb heat from (or alternatively, transfer heat to) blood passing along the exterior of the rotating fiber bundle.

Methods of using the integrated system of the present invention are also provided.

BRIEF DESCRIPTION OF THE DRAWINGS

Further features of the invention, its nature and various advantages will be more apparent from the accompanying drawings and the following detailed description of the preferred embodiments, in which.

DETAILED DESCRIPTION OF THE INVENTION

The present invention provides an integrated blood oxygenator, pump, and heat exchanger system that combines active blood oxygenation using a rotating fiber bundle with a large heat transfer area and high pumping head, thereby overcoming the drawbacks of previously known devices. In accordance with the principles of the present invention, the device may be placed in or near the sterile field and preferably has a low priming volume, e.g., 200 cc or less.

Figure 1:
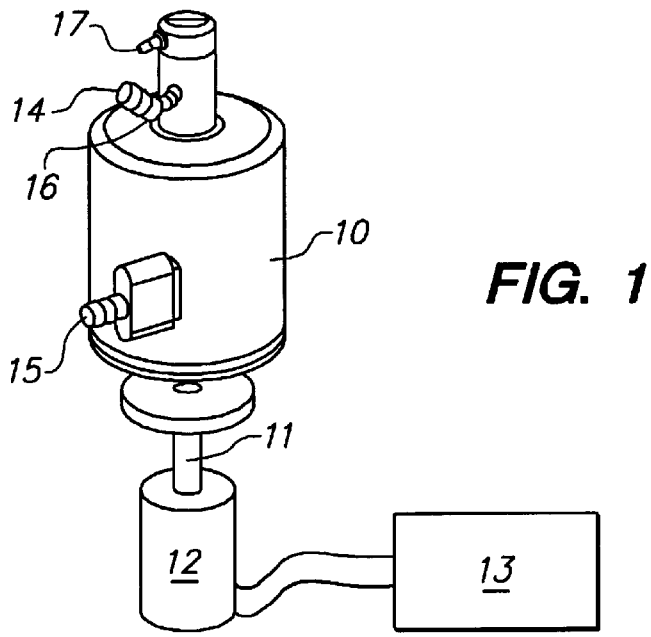
FIG. 1 is a perspective view of an integrated blood oxygenator and pump system suitable for implementing the present invention.
Figure 2A:
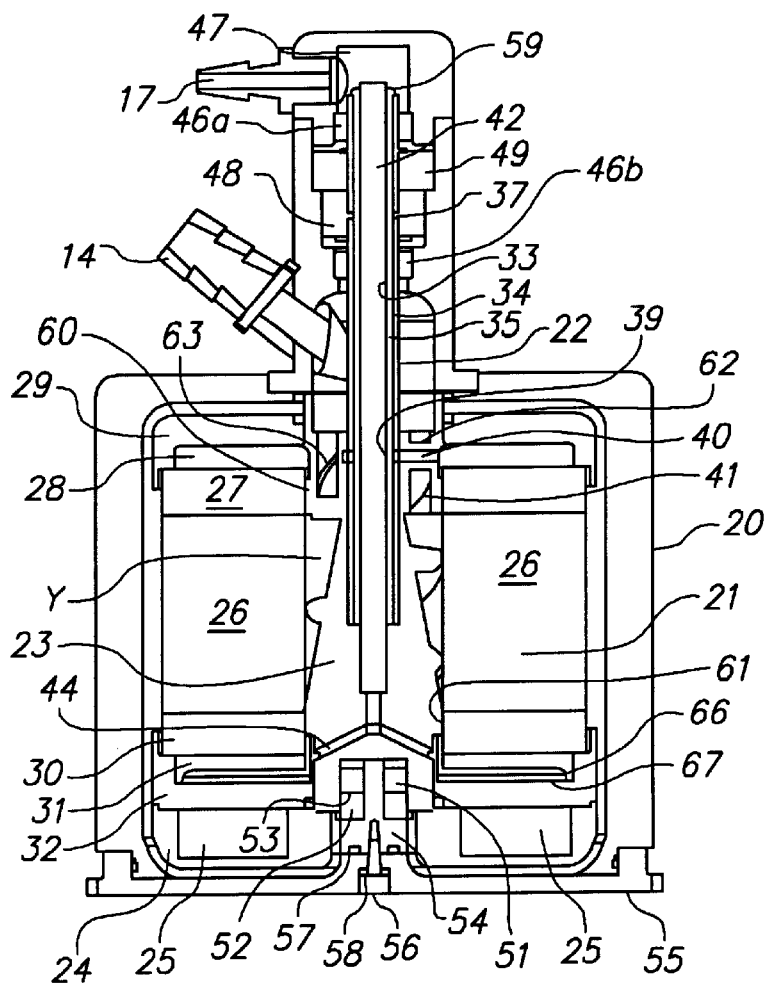
FIGS. 2A and 2B are, respectively, side-sectional and cut-away views of the device of FIG. 1.

Referring to FIGS. 1, 2A and 2C, an integrated blood oxygenator/pump 10 suitable for implementing a device in accordance with the principles of the present invention is described. Pump/oxygenator 10 is of the type described in co-pending, commonly assigned U.S. patent application Ser. No. 09/223,676, filed Dec. 30, 1998, which is incorporated herein by reference, and includes several improvements over the previously known rotating fiber bundle designs.

Pump/oxygenator 10 is magnetically coupled to drive shaft 11 of motor 12, which is in turn controlled by controller 13. Deoxygenated venous blood is supplied to pump/oxygenator 10 via suitable biocompatible tubing (not shown) coupled to venous blood inlet 14; oxygenated blood passes out of pump/oxygenator 10 through blood outlet 15. Pressurized oxygen is introduced into pump/oxygenator 10 via gas inlet port 16, while a mixture of oxygen and carbon dioxide exits pump/oxygenator 10 via gas outlet port 17. Alternatively, gas may be introduced into device 10 with a reversed flow path, i.e., gas outlet port 17 is used as the gas inlet and gas inlet port 16 is used as the gas outlet.

Motor 12, magnetically coupled drive shaft 11 and controller 13 are items per se known in the art, and may comprise any of a number of systems available from Bio-Medicus, Inc., Eden Prairie, Minnesota. Alternatively, drive shaft 11, motor 12 and controller 13 may be miniaturized to permit their placement closer to the patient.

Figure 2B:
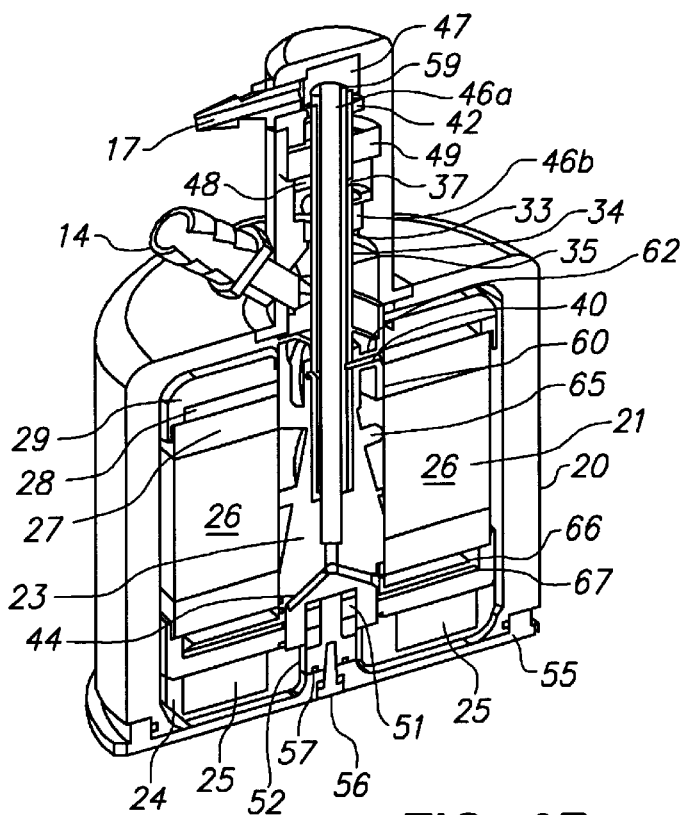

Referring now to FIGS. 2A and 2B, pump/oxygenator 10 comprises housing 20 enclosing fiber bundle assembly 21 that rotates within housing 20 on shaft 22. Shaft 22 is affixed to shaft impeller 23, which is attached to tray 24. Tray 24 holds one or more magnets 25 that are used to magnetically couple fiber bundle assembly 21 to drive shaft 11.

Fiber bundle 26 preferably comprises a multiplicity of microporous hollow fiber elements having an upper end potted in region 27, so that the interior lumens of the fibers communicate with plenum 28 in inlet gas manifold 29. Likewise, the lower ends of the hollow fiber elements of fiber bundle 26 are potted in region 30, so that the interior lumens of the fibers communicate with plenum 31 in outlet gas manifold 32. Any of a number of suitable biocompatible potting materials may be used, such as polyurethanes or epoxies.

Shaft 22 includes inner tube 33 and outer tube 34 arranged coaxially to form annulus 35. Annulus 35 communicates with gas inlet port 16 (see FIG. 1) via through-wall holes 37, and with plenum 28 of inlet gas manifold 29 via through-wall holes 39 and passageways 40 in plurality of pumping vanes 41. Lumen 42 of inner tube 33 communicates with gas outlet port 17 at its upper end and plenum 31 in outlet gas manifold 32 at its lower end via passageways 44 in shaft impeller 23. Shaft seal 46a separates space 47, which couples gas outlet port 17 to lumen 42, from space 48, which couples gas inlet port 16 (see FIG. 1) to annulus 35. Shaft seal 46b separates space 48 from the interior of housing 20, which encloses fiber bundle assembly 21.

Shaft 22 is carried in bearing 49, while shaft impeller 23 is carried on bearings 51 and 52. Thrust washer 53 is interposed between bearings 51 and 52, and the entire assembly is in turn carried on bearing shaft 54. Bearing shaft 54 is affixed to lower plate 55 of housing 20 by shoulder screw 56, and is seated on O-ring seal 57. Shoulder screw 56 also is sealed with O-ring 58. Shaft impeller 23 seals the lower end of annulus 35, while the upper end of the annulus is sealed by plug 59.

Shaft impeller 23 (see FIG. 2B) has upper hub 60 and lower hub 61. Upper hub 60 is connected to upper potting 27 and lower hub 61 is connected to lower potting 30. Pumping vanes 62 extend between annulus 23 and upper hub 60, and openings 63 between the plurality of vanes 62 permit blood entering pump/oxygenator 10 via venous blood inlet 14 to flow into void V of fiber bundle 26. Vanes 62 are configured to serve as vanes that pump and accelerate blood passing through the fiber bundle 26. Optionally, shaft impeller 23 may include spiral vanes 65 between upper hub 60 and lower hub 61.

Baffle plate 66 is disposed in plenum 31, and includes grooves 67 on its underside that communicate with passageways 44. Baffle plate 66 thus causes gas exiting fiber bundle 26 to pass around the outermost edge of the baffle plate. Accordingly, blood leaking into plenum 31 of outlet gas manifold 32 is cleared from the manifold and entrained in the exhaust gas stream passing through gas outlet port 17.

Figure 3:
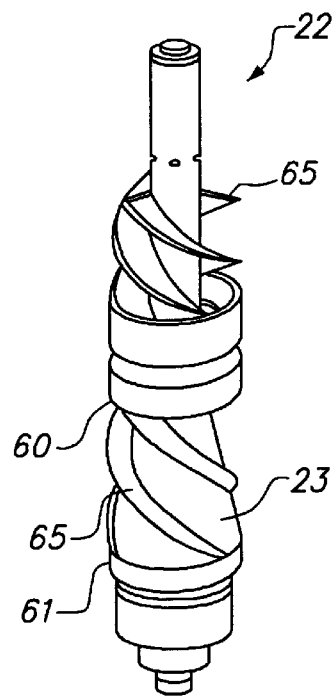
FIG. 3 is a partial view of alternative embodiment of a central shaft suitable for use in the device of FIG. 1.

FIG. 3 shows an alternative embodiment of shaft impeller 23, where helical vanes 65 extend above hub 60 to further augment the pump head developed by rotation of shaft impeller 23 and fiber bundle 26. As will of course be appreciated, the pump housing and seal locations must be appropriately modified to accommodate extended vanes 65 of FIG. 3.

As described in the above-incorporated application, the construction of pump/oxygenator 30 includes a number of advantageous features relative to previously-known rotating fiber bundle systems, including reduced microbubble generation, reduced shear-induced blood trauma, reduced flooding associated with fiber breakage, and reduced stress-induced failure of fibers. Further descriptions of those advantages may be found in the above-incorporated application.

Figure 4:
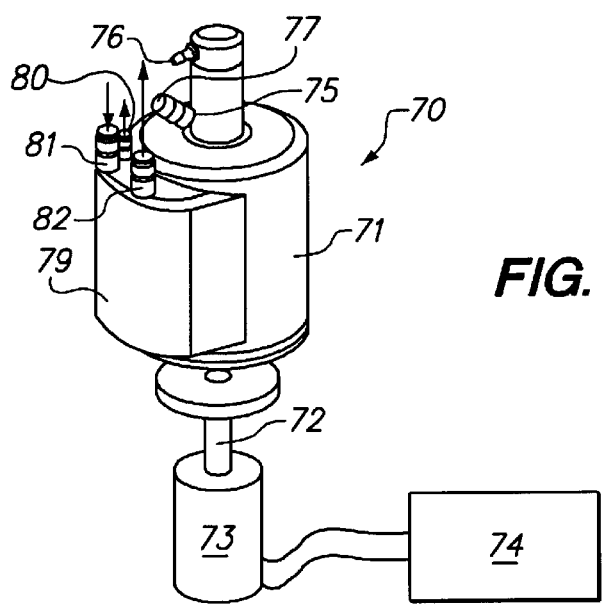
FIG. 4 is a perspective view of an integrated oxygenator, pump and heat exchanger constructed in accordance with the present invention.

Referring now to FIG. 4, integrated apparatus 70 constructed in accordance with the principles of the present invention is described. Device 70 includes a pump/oxygenator component within housing 71 that is similar in construction to pump/oxygenator 10 of FIG. 1. Device 70 in addition includes an integrated heat exchanger that overcomes drawbacks associated with heat exchangers used in previously known rotating fiber bundle pump/oxygenators.

In particular, device 70 is magnetically coupled to drive shaft 72 of motor 73, which is in turn controlled by controller 74. Pressurized oxygen is introduced into housing 71 via gas inlet port 75, while a mixture of oxygen and carbon dioxide exits housing 71 via gas outlet port 76. Deoxygenated venous blood is supplied to device 70 through venous blood inlet 77; oxygenated blood passes out of housing 71 and into heat exchanger 79. Heated, oxygenated blood passes out of device 70 via blood outlet 80.

Heat exchange fluid, e.g. water, enters heat exchanger 79 at fluid inlet 81 at a user-selected flow rate and heat content. The fluid exchanges thermal energy with the oxygenated blood inside heat exchanger 79 en route to fluid outlet 82. By varying the inlet temperature and flow rate of the coolant, the oxygenated blood may be regulated to a desired temperature before exiting heat exchanger 79 before the blood is returned to the patient via blood outlet 80. As will be apparent to one skilled in the art of heat exchanger design, temperature regulation alternatively may be achieved prior to oxygenating the blood, or at multiple points along the blood flow path.

Figure 5A:
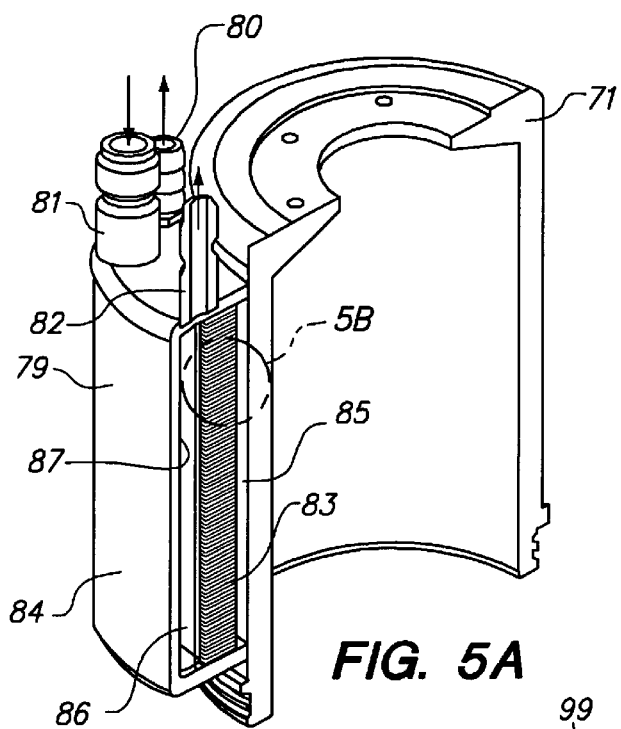
FIGS. 5A and 5B are, respectively, a cut-away view of a first illustrative embodiment of a heat exchanger portion of the device of FIG. 4, and a detailed side view of the pleated wall of the device of FIG. 5A.
Figure 5B:
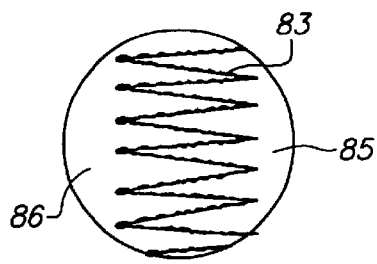

Referring now to FIGS. 5A and 5B, an illustrative embodiment of heat exchanger 79 of FIG. 4, is described. Heat exchanger 79 comprises pleated stainless steel wall 83 disposed in housing 84 using suitable biocompatible potting material to form blood side compartment 85 and coolant side compartment 86. Additionally, as illustrated in FIG. 5B, wall 83 may itself be corrugated to further increase the heat transfer area. As will be appreciated by those familiar with heat exchanger design, the pleating of wall 83 increases the overall area for heat transfer. As will further be appreciated, coolant side 86 of heat exchanger may be used to either transfer heat to, or absorb heat from, blood in contact with the blood side of wall 83, depending upon the temperature of the fluid introduced into coolant side compartment 86.

Heat exchanger fluid, e.g. water, flows into heat exchanger 79 via fluid inlet 81, and travels through coolant side compartment 86 along a serpentine path to fluid outlet 82. This serpentine path may be accomplished, for example, using ribs that extend inwardly from wall 87 of coolant side compartment 86, to ensure that coolant passing through coolant side compartment 86 contacts the coolant side of pleated wall 83. Alternatively, such ribs may be omitted, and stagnation zones within coolant side compartment 86 reduced by passing the coolant through the compartment at a relatively high flow rate.

Oxygenated blood enters blood side compartment 85 via a through-wall opening between heat exchanger housing 84 and housing 71. Alternatively, blood outlet 15, as shown in FIG. 1, may be provided in housing 70, and a separate piece of tubing used to couple the blood outlet to a blood inlet (not shown) of heat exchanger 79. The blood then travels through blood side compartment 85 to blood outlet 80.

Pleated wall 83 preferably is formed from a thin sheet of a highly conductive material, e.g. stainless steel, that has been bent back and forth upon itself to create a pleated structure with a large surface area composed of small channels. The channels are accessible on alternating sides of wall 83, so that blood in contact with wall 83 in blood side compartment 85 flows through the channels interdigitated with channels through which heat exchanger fluid in coolant side compartment 86 flows, and vice versa. Over a large surface area, the blood and heat exchanger fluid are only separated by the highly conductive, thin metal sheet, thereby enabling efficient thermal energy transfer.

Figure 6A:
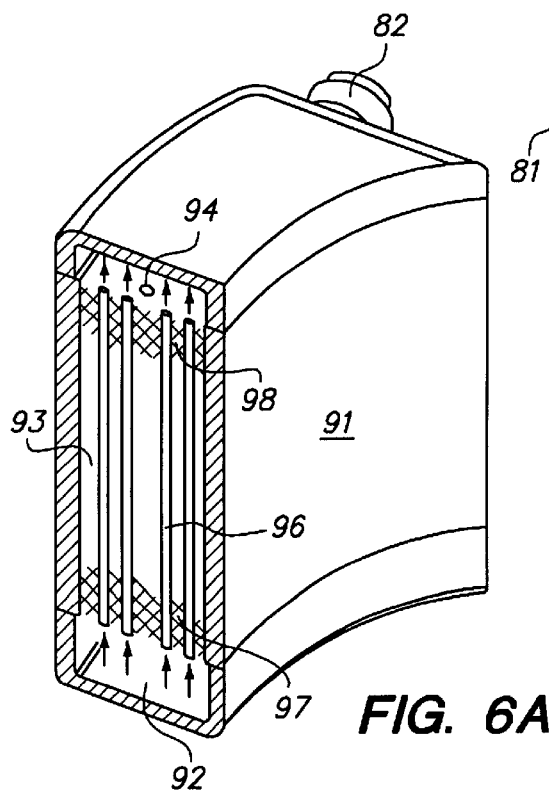
FIGS. 6A and 6B are, respectively, a side-sectional view and a partial perspective view of an alternative embodiment of the heat exchanger portion of the device of FIG. 4.
Figure 6B:
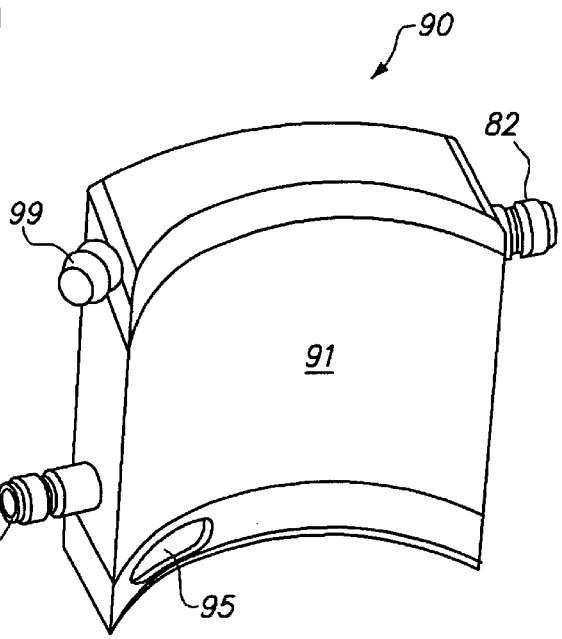

With reference to FIGS. 6A and 6B, an alternative embodiment of a heat exchanger element constructed in accordance with the present invention is described. Heat exchanger 90 includes housing 91 which may be coupled to or integrally formed with the housing 71. Housing 91 includes lower plenum 92, heat transfer region 93, upper plenum 94, and blood inlet 95. Bundle 96 of non-permeable hollow fibers (only a few of which are depicted in FIG. 6A) is potted in tube sheets 97 and 98 at either end of heat transfer region 93.

As indicated by the arrows in FIG. 6A, oxygenated blood enters lower plenum 92 through inlet 95, passes through bundle 96 of hollow fibers and exits into upper plenum 94, and is returned to the patient via blood outlet 99. Heat transfer fluid, e.g. water, flows through fluid inlet 81 into heat transfer region 93, where it contacts the exterior surfaces of the fibers carrying oxygenated blood. The heat transfer fluid exits heat transfer region 93 via fluid outlet 82.

Advantageously, because heat exchanger 90 constitutes an integral part of the overall device, the pressure drop imposed by heat exchanger 90 may be readily accounted for in developing flow rate versus bundle angular velocity characteristic curves. In this way, the blood flow rate at the output of the heat transfer provided by the device may be empirically determined as a function of the bundle angular velocity. This information may in turn be used to generate flow rate profiles for controller 74 (see FIG. 4) as a function of bundle angular velocity.

Figure 7A:
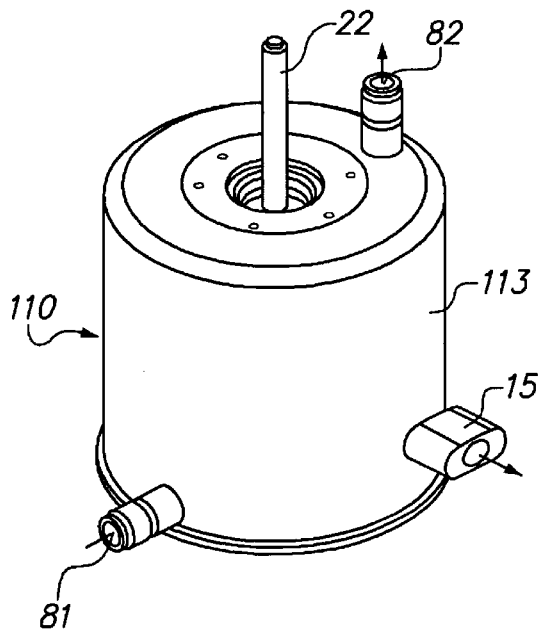
FIGS. 7A–7C are, respectively, a partial perspective exterior view, side-sectional view, and perspective cut-away view of an alternative embodiment of the device of the present invention.
Figure 7B:
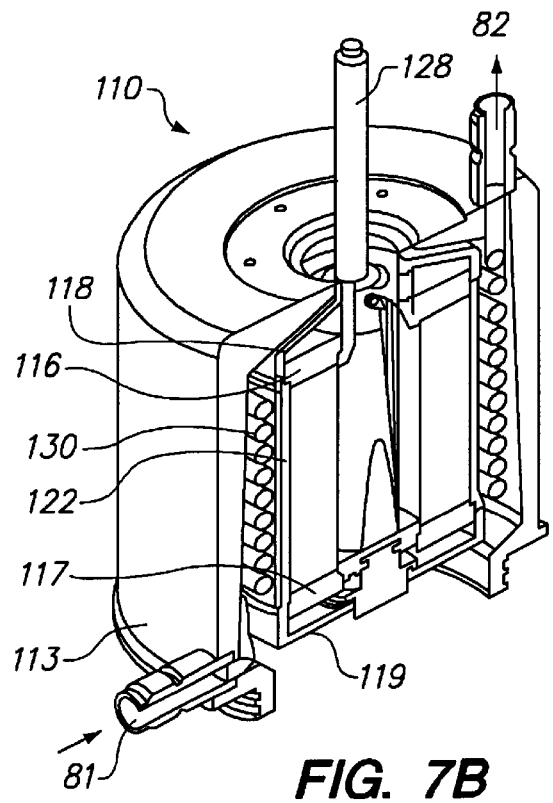
Figure 7C:
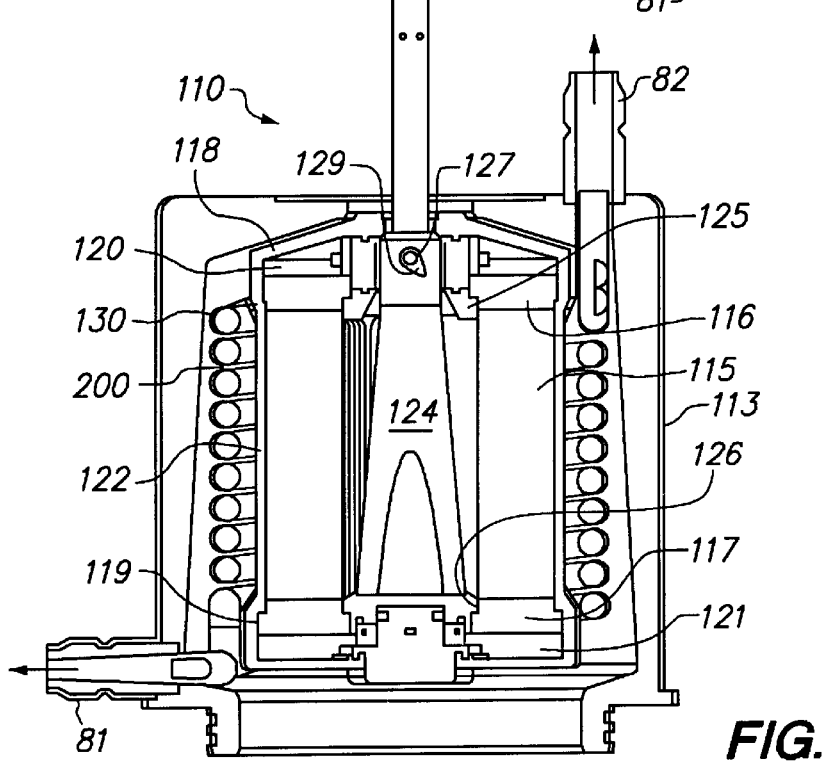

Referring now to FIGS. 7A–7C, another alternative embodiment of an integrated apparatus constructed in accordance with the principles of the present invention is described. In FIG. 7A, a portion of integrated device 110 is shown, from which the upper portion of housing 113 has been omitted (compare to FIG. 2A). In this embodiment, heat transfer fluid enters through fluid inlet 81 and exits through fluid outlet 82 after passing through a coiled tubing, described hereinbelow. Blood entering device 110 via the venous inlet on the upper portion of housing 113 (not shown) exits the device via blood outlet 15.

With respect to FIGS. 7B and 7C, integrated device 110 includes annular fiber bundle 115 potted in regions 116 and 117 in manifolds 118 and 119, respectively. Manifolds 118 and 119 define inlet plenum 120 and outlet plenum 121, and are mounted at the peripheries in rigid perforated sidewall 122, which constrains outward bowing of the fibers in bundle 115. Impeller shaft 124 is coupled to inner cage 125 that is in turn coupled to potting regions 116 and 117 and lower hub 126. Tubes 127 conduct gas from an annulus within shaft 128, and include tear-drop shaped elements 129 that swing freely over tubes 127. Elements 129 automatically adjust position responsive to changes in rotational speed of fiber bundle 115 and blood flow, thereby reducing trauma caused to blood contacting tubes 127. Operation of annular fiber bundle 115 is similar to that described hereinabove for the device of FIGS. 2A and 2B.

In accordance with the present invention, the heat exchanger of apparatus 110 comprises coiled tube 130 disposed within housing 113. Coiled tubing 130 preferably is fabricated from a highly conductive material, such as copper or a steel alloy. Coiled tubing 130 is spaced apart from annular fiber bundle 115 so that a gap exists between sidewall 122 and the interior surface of the coil when the fiber bundle is rotated. Preferably, there is also a gap between the exterior surface of the coiled tube and the inner surface of housing 113 to prevent the development of stagnation zones. Adjacent turns of coiled tube 130 include small gaps 200, so that blood exiting the fiber bundle contact and pass through the turns of the coiled tube.

In operation, as impeller shaft 124 rotates, deoxygenated blood is forced through fiber bundle 115 by centrifugal force. The blood is oxygenated in the fiber bundle and then flows around coiled tubing 130 before exiting through blood outlet 15 and being returned to the patient. Efficient thermal energy transfer occurs between the heat transfer fluid in coiled tubing 130 and the oxygenated blood exiting fiber bundle 115. By varying the inlet temperature and flow rate of coolant introduced at fluid inlet 81, blood oxygenated and pumped by integrated apparatus 110 may be regulated.

The integrated device of the present invention illustratively has been described as employing a magnetic coupling, as shown in FIGS. 1 and 4. The present invention, however, may be readily adapted for use with other drive systems. For example, the magnet tray may be replaced with a direct motor drive, or may be coupled by a cable to a drive system and control console located outside the sterile field. Such a direct drive system could be miniaturized to be accommodated within the sterile field. Furthermore, the controls could be operated remotely using infrared or other such remote controlling means. The integrated blood pump, oxygenator and heat exchanger of the present invention also may be incorporated into a standard cardiopulmonary bypass system that has other standard components such as a heat exchanger, venous reservoir, arterial filter, surgical field suction, cardiac vent, etc.

While preferred illustrative embodiments of the invention are described above, it will be apparent to one skilled in the art that various changes and modifications may be made therein without departing from the invention and it is intended in the appended claims to cover all such changes and modifications which fall within the true spirit and scope of the invention.

What is claimed is:

1. A system for processing blood comprising:
   a housing having an interior wall, a gas inlet, a gas outlet, a blood inlet, a blood outlet, a coolant inlet and a coolant outlet;
   a shaft disposed within the housing;
   an annular bundle of hollow fibers disposed for rotation on the shaft, the annular bundle having a first end in fluid communication with the gas inlet, a second end in fluid communication with the gas outlet, and a central void in fluid communication with the blood inlet;
   a plurality of vanes disposed within the central void and affixed to the shaft; and
   a heat exchanger element having an exterior surface disposed within the housing between the annular bundle and the interior wall of the housing, an interior of the heat exchanger element in fluid communication with the coolant inlet and the coolant outlet,
   wherein rotation of the annular bundle causes blood received within the central void to pass outward through the annular bundle, flow around the exterior surface of the heat exchanger element, and exit through the blood outlet.

2. The apparatus of claim 1 wherein the heat exchanger element comprises a coiled tube that surrounds the annular bundle.

3. The apparatus of claim 2 wherein the coiled tube comprises a plurality of adjacent turns spaced apart relative to one another to form gaps.

4. The apparatus of claim 1 further comprising a first plurality of vanes that accelerate blood prior to entry into the central void.

5. The apparatus of claim 4 wherein the first plurality of vanes is mounted on the shaft.

6. A method for processing blood comprising:
   providing apparatus comprising a housing having a gas inlet and a gas outlet, a coolant inlet and a coolant outlet, a blood inlet and a blood outlet, an annular bundle of hollow fibers disposed on a shaft for rotation within the first housing and having a first end in fluid communication with the gas inlet, a second end in fluid communication with the gas outlet, and a central void, a plurality of vanes disposed within the central void and affixed to the shaft, and a heat exchanger in fluid communication the coolant inlet and the coolant outlet;
   causing blood to flow into the housing and the central void;
   rotating the plurality of vanes;
   causing a gas comprising oxygen to flow through the hollow fibers of the annular bundle;
   rotating the annular bundle to oxygenate blood flowing through the housing and to develop sufficient pressure head to cause the oxygenated blood to flow through the heat exchanger; and transferring heat to or from blood flowing through the heat exchanger.

7. The method of claim 6 wherein the apparatus further comprises a first plurality of vanes that accelerate blood prior to entry into the central void, the method further comprising rotating the first plurality of vanes.

8. The method of claim 7 wherein the first plurality of vanes is mounted to the shaft and are rotated at an angular velocity identical to an angular velocity of the annular bundle.

9. The method of claim 6 wherein heat exchanger comprises a coiled tube disposed within the housing surrounding the annular bundle, and transferring heat to or from blood flowing through the heat exchanger comprises causing the blood to contact an exterior surface of the coiled tube.

10. A method for processing blood comprising:

providing apparatus comprising a housing having a gas inlet and a gas outlet, a coolant inlet and a coolant outlet, a blood inlet and a blood outlet, an annular bundle of hollow fibers disposed on a shaft for rotation within the first housing and having a first end in fluid communication with the gas inlet, a second end in fluid communication with the gas outlet, and a central void, a first plurality of vanes that accelerate blood prior to entry into the central void, and a heat exchanger in fluid communication the coolant inlet and the coolant outlet;

causing blood to flow into the housing;

rotating the first plurality of vanes;

causing blood to flow into the central void;

causing a gas comprising oxygen to flow through the hollow fibers of the annular bundle;

rotating the annular bundle to oxygenate blood flowing through the housing and to develop sufficient pressure head to cause the oxygenated blood to flow through the heat exchanger; and transferring heat to or from blood flowing through the heat exchanger.

11. The method of claim 10, wherein the heat exchanger comprises a coiled tube disposed within the housing surrounding the annular bundle, and transferring heat to or from blood flowing through the heat exchanger comprises causing the blood to contact an exterior surface of the coiled tube.

12. The method of claim 10, wherein the apparatus further comprises a plurality of vanes disposed within the central void and affixed to the shaft, the method further comprising rotating the plurality of vanes.

13. The method of claim 10, wherein the first plurality of vanes is mounted to the shaft and are rotated at an angular velocity identical to an angular velocity of the annular bundle.

* * * * *